United States Patent [19] [11] Patent Number: 4,999,090
Tateno et al. [45] Date of Patent: Mar. 12, 1991

[54] PROCESS FOR PREPARING TRANS-1,4-CYCLOHEXANEDIMETHANOL AND POWDER OF THE SAME

[75] Inventors: Yoshiaki Tateno, Omiya; Susumu Yoneda, Fuji; Naoki Okamoto, Fuji; Yoshibumi Ishii, Fuji; Kazuaki Kato, Yoshikawamachi, all of Japan

[73] Assignee: Towa Chemical Industry Co., Ltd., Tokyo, Japan

[21] Appl. No.: 375,493

[22] Filed: Jul. 5, 1989

[30] Foreign Application Priority Data

Apr. 10, 1988 [JP] Japan .................................. 1-87991
Aug. 1, 1988 [JP] Japan ................................ 63-190726
Dec. 27, 1988 [JP] Japan ................................ 63-327811

[51] Int. Cl.$^5$ ........................ B01D 3/10; B01D 3/34
[52] U.S. Cl. ...................................... 203/36; 203/91; 203/DIG. 6; 568/822; 568/831
[58] Field of Search ................. 203/36, 91, DIG. 6; 202/205; 241/17; 568/822, 831; 110/232, 341; 159/47.1, DIG. 16, DIG. 23

[56] References Cited

U.S. PATENT DOCUMENTS

| | | | |
|---|---|---|---|
| 1,997,937 | 4/1935 | Léauté | 62/499 |
| 2,917,549 | 12/1959 | Hasek et al. | 568/831 |
| 3,379,624 | 4/1968 | Lindkvist | 568/831 |

FOREIGN PATENT DOCUMENTS

| | | | |
|---|---|---|---|
| 0664232 | 6/1963 | Canada | 568/831 |
| 0677552 | 1/1964 | Canada | 568/831 |
| 0721329 | 11/1965 | Canada | 568/831 |
| 0879264 | 10/1961 | United Kingdom | 568/831 |
| 0902372 | 8/1962 | United Kingdom | 568/831 |
| 0988012 | 3/1965 | United Kingdom | 568/831 |

OTHER PUBLICATIONS

"Journal of Liquid Chromatography", 10(6), pp. 1077–1084 (1987).
"Journal of The Chemical Society", pp. 404–407, (1953).
"Acta Pharmaceutica", Saecica 5 pp. 449–456 (1968).

Primary Examiner—Virginia Manoharan
Attorney, Agent, or Firm—Beveridge, DeGrandi & Weilacher

[57] ABSTRACT

A process of preparing industrially trans-1,4-cyclohexanedimethanol of high purity by distilling a mixture of cis- and trans-1,4-cyclohexanedimethanol in the presence of alkali, or by heating a mixture of cis- and trans-1,4-cyclohexanedimethanol in the presence of alkali and then distilling the heated mixture, and a process of preparing powdered trans-1,4-cyclohexanedimethanol by pulverizing the distillate obtained above.

9 Claims, No Drawings

PROCESS FOR PREPARING TRANS-1,4-CYCLOHEXANEDIMETHANOL AND POWDER OF THE SAME

BACKGROUND OF THE INVENTION

The present invention relates to a process of preparing trans-1,4-cyclohexanedimethanol and powder of the same, which is useful as raw material for polyester resin, polyester synthetic fiber, polyester coating material and the like, or as chemical intermediates.

1,4-cyclohexanedimethanol (hereinafter may be referred to as 1,4-CHDM) is industrially prepared by distillation, for example, by hydrogenating 1,4-cyclohexanedicarboxylic acid dimethylester in the presence of copper-chromium catalyst and then distilling the hydrogenated compound.

1,4-CHDM thus prepared comprises usually about 70% by weight of trans-1,4-CHDM and about 30% by weight of cis-1,4-CHDM, and, this product is waxy or mascuite-like at room temperatures.

The melting point of cis-1,4-CHDM of high purity is lower than room temperature, and it is liquid at room temperatures; on the contrary, the melting point of trans-1,4-CHDM of high purity is 60° to 64° C. and it is solid at room temperatures.

Polyester resins made from trans-1,4-CHDM have high glass transition temperatures and high softening points, and they are superior in the properties of the resin. Therefore, trans-1,4-CHDM is preferable as the raw material of polyester products.

Conventional processes of preparing trans-1,4-CHDM are shown below:

(a) a mixture of cis-and trans-1,4-CHDM is converted in trimethylsilyl compound and the compound is separated by diglycerol column chromatography, as disclosed in Acta Pharmaceutica Suecica 5(5), pp 449–456(1968).

(b) A mixture of cis- and trans-1,4-CHDM is separated by cyclodextrine-combined silica gel column chromatography, as disclosed in Journal of Liquid Chromatography 10(6) pp 1077–1084(1987).

(c) A mixture of cis- and trans-1,4-CHDM is converted to dibenzoate compound, and the compound is selectively crystallized by utilizing the difference of crystallization and then hydrolyzed to obtain trans-1,4-CHDM, as disclosed in Journal of the Chemical Society pp 404–407(1953).

However, according to the conventional processes described above, high purity trans-1,4-CHDM may be obtained only in small amounts by the distillation, and the majority of distillate is a mixture of trans- and cis-1,4-CHDM containing about 30% of cis-1,4-CHDM, the mixture having a melting point of about 40° C.

1,4-CHDM containing about 30% of cis-1,4-CHDM has the disadvantages described below.

For example, in the case of commercial transportation, expensive drums are needed, because the compound is waxy or mascuite-like. This compound requires previous heating at temperatures of 50°–60° C. prior to its use, and it is decomposed or colored by heating or melting, therefore its use is restricted. Heating or melting is expensive and therefore, the product made from it becomes more costly to produce. Thus, there are a lot of disadvantages.

Further, the conventional processes of preparing trans-1,4-CHDM as shown in examples (a)–(c) above are analytical processes or laboratory processes. These processes suffer from many disadvantages, such as: low yield, high production costs, and complicated manufacturing processes. Therefore, the conventional processes are not fit for commercial production, and they are not satisfactory for producing trans-1,4-CHDM or powders thereof.

SUMMARY OF THE INVENTION

In view of the above-mentioned background, it is desired to obtain commercially useful trans-1,4-CHDM and powdered trans-1,4-CHDM.

The inventors found that high purity trans-1,4-CHDM can be obtained in good yield by distilling a mixture of cis- and trans-1,4-cyclohexanedimethanol in the presence of alkali, or by heating a mixture of cis-and trans-1,4-cyclohexanedimethanol in the presence of alkali and then distilling the mixture, and powdered trans-1,4-CHDM can be obtained by pulverizing the distillate. The present invention is based on this discovery.

The mixture of cis- and trans-1,4-CHDM used in this invention can be obtained by the conventional processes.

In this invention, a solvent such as water, methanol and ethanol may be used, and a solution of 1,4-CHDM having a concentration of 50 to 100% by weight is preferably used. However, the reaction can be carried out more preferably in the absence of solvent.

Alkali compounds used in this invention are hydroxides of alkali metals such as sodium, potassium and lithium, hydroxides of alkaline earth metals, alcoholates such as sodium methoxide and sodium ethoxide, and amines such as ethanolamine.

Alkali compounds are used preferably in an amount of 0.1 to 5% by weight to the amount of 1,4-CHDM. When the alkali compounds are used in an amount of less than 0.1%, trans-1,4-CHDM may be obtained in a smaller amount, and when the alkali compounds are used in an amount of more than 5%, ether-linked polymers are obtained.

The alkali compound may be added in powder form. However, alkali compounds are added preferably as a solution with a small amount of water or organic solvents, or in a solution of alcoholates, because alkali compounds are slightly soluble in 1,4-CHDM.

The alkali compounds may be added before distillation or during distillation.

After the distillate containing trans-1,4-CHDM in a high percentage is obtained by adding the alkali compounds during distillation, alkali compounds may be added further and the mixture is heated to obtain trans-1,4-CHDM by distillation.

On the other hand, the alkali compounds are added before distillation and the mixtue is heated under the following conditions:

HEATING TEMPERATURE

150° to 250° C., preferably 160° to 200° C.

When the reaction is carried out at a temperature of lower than 150° C., a long reaction time is required to obtain a large amount of trans-1,4-CHDM.

When the reaction is carried out at a temperature of higher than 250° C., either-linked-by-products are produced in a large amount.

REACTION TIME

The reaction time is dependent upon the heating temperature, the kind of alkali and the amount thereof. For example, when the reaction is carried out for one hour at a temperature of 160° C. and in the concentration of 2% by weight of alkali, or when the reaction is carried out for 30 minutes at a temperature of 200° C. and in the concentration of 0.5% by weight of alkali, trans-1,4-CHDM can be obtained in the largest amount.

The distillation is carried out preferably at temperatures of 150° to 200° C. under a reduced pressure of 1 to 50 mmHg.

The distillation may be carried out under reduced pressure of lower than 1 mmHg or higher than 50 mmHg. When the pressure is lower than 1 mmHg, expensive equipment is required, and when the pressure is higher than 50 mmHg, higher temperatures for distillation are required, and decomposition or etherification occurs.

For example, when 1,4-cyclohexanedicarboxylic acid dimethylester is reduced in the presence of copper-chromium catalyst to obtain reaction products containing principally 1,4-CHDM, the products usually contain about 70% of trans-1,4-CHDM. When said reduction is carried out in the presence of 0.5% by weight (per reaction mixture) of NaOH at a temperature of 180° C. for about 60 minutes, products containing about 85% of trans-1,4-CHDM can be obtained, and further, products containing about 90% of trans-1,4-CHDM can be obtained by distillation.

On the other hand, when alkali is added at the distillation, the product containing about 95% of trans-1,4-CHDM can be obtained in a yield of 95%.

The distillation can be carried out by batch or continuous distillation, and preferably by continuous distillation with a rectification tower having a "number of theoretical plates" of ten to twenty plates.

1,4-CHDM containing about 85% of trans-1,4-CHDM has a melting point of about 60° C., and it is a hard solid at low temperatures. Therefore, powdered 1,4-CHDM can be obtained by kneading and shaping under cooling 1,4-CHDM containing prevailingly trans-1,4-CHDM or by cooling the 1,4-CHDM to a solid state and then cutting it.

Polyester resins and derivatives thereof having superior qualities such as a higher glass transition point can be prepared by using 1,4-CHDM or powdered 1,4-CHDM containing prevailingly trans-1,4-CHDM.

Higher heat-stable polyester copolymer can be obtained by allowing to react glycol containing 50 to 97 mol % of 1,4-CHDM containing 80% or more of trans-1,4-CHDM, preferably 90% or more of trans-1,4-CHDM, and glycol containing 3 to 50 mol % of ethylene glycol with a dicarboxylic acid such as terephthalic acid, in comparison with polyester copolymer obtained by using 1,4-CHDM containing less than 80% of trans-1,4-CHDM.

In the preparation of the polyester copolymer mentioned above, if necessary, fiber reinforcing agent, flame retarder, coloration-preventing agent, antistatic agent, heat-resisting agent, weather proofing agent and the like can be added to improve the qualities of polyester resins obtained and the derivatives thereof.

Consequently, derivatives such as polyester resins having superior qualities in heat resistance, fire resistance, weather-proofing property, deformation resistance, antistatic property and the like can be prepared by using trans-1,4-CHDM or powders thereof obtained by the process of the present invention or by adding thereto various agents as shown in the above discussion.

As mentioned above, trans-1,4-CHDM can be prepared at less expense and high yield by the process of the present invention.

By the present invention, powdered trans-1,4-CHDM can be made economically on a commercial scale. The product is a solid at room temperatures, easy to handle and capable of storage in a cheap container.

Further, by using trans-1,4-CHDM or powders thereof obtained in the present invention or by using the products obtained by adding various improving agents, derivatives such as polyester resins having superior qualities in heat resistance, fire resistance, weather resistance, deformation resistance, antistatic property and the like can be manufactured, and consequently the range of use of 1,4-CHDM can be increased.

DESCRIPTION OF THE PREFERRED EMBODIMENTS

The present invention will be illustrated by the following examples. The examples are not intended to limit the scope of the present invention.

PREPARATION OF RAW MATERIALS (1,4-CHDM)

250 kg of 1,4-cyclohexanedicarboxylic acid dimethylester and 25 kg of copper-chromium catalyst (C-5, manufactured by Sakai Chemical Co., Ltd.) were agitated in an autoclave (volume: 550 liter) at a temperature of 260° C., and after hydrogen had been absorbed the catalyst was filtered off. The filtrate obtained was distilled to obtain Raw material (a) and Raw material (b).

Raw material (a) and Raw material (b) were analyzed by gas chromatography. Raw material (a) comprises 45% of cis-1,4-CHDM and 55% of trans-1,4-CHDM, and Raw material (b) comprises 26% of cis-1,4-CHDM and 74% of trans-1,4-CHDM.

Raw material (a) is rice cake like, and Raw material (b) is a waxy solid. Both materials (a) and (b) cannot be crushed.

EXAMPLE 1

A mixture of 50 g of Raw material (a) and 2 g of a 50% aqueous solution of NaOH was put in an eggplant type flask of 100 ml and was heated in an oil bath at a temperature of 180° C. for 30 minutes, while stirring, and then cooled to room temperature to obtain Substance A including prevailingly trans-1,4-cyclohexanedimethanol.

Substance A comprises 15.4% of cis-1,4-CHDM and 84.6% of trans-1,4CHDM (by chromatographic analysis).

Substance A was distilled under the conditions of "number of thertical plates" of 20 plates, reduced pressure of 10 mmHg and temperatures of 152° to 163° C. to obtain 30 g of Distillate Aa, which comprises 3.1% of cis-1,4-CHDM and 96.9% of trans-1,4-CHDM.

EXAMPLE 2

A mixture of 50 g of Raw material (a) and 0.2 g of a 50% aqueous solution of NaOH was put in an eggplant type of flask of 100 ml and was heated in an oil bath at a temperature of 200° C. for three hours, while stirring, and then cooled to room temperature to obtain Substance B including prevailingly trans-1,4-cyclohexanedimethanol.

Substance B comprises 17.7% of cis-1,4-CHDM and 82.3% of trans-1,4-CHDM.

Substance B was distilled under the same conditions as shown in Example 1 except that it was distilled under the conditions of reduced pressure of 40 mmHg and temperatures of 185° to 188° C. 30 g of Distillate Ba was obtained, which comprises 3.9% of cis-1,4-CHDM and 96.1% of tran-1,4-CHDM.

EXAMPLE 3

A mixture of 50 g of Raw material (a) and 1.0 g of a 20% aqueous solution of NaOH was put in an eggplant type flask of 100 ml and was heated in an oil bath at a temperature of 160° C. for two hours, while stirring, and then cooled to room temperature to obtain Substance C prevailingly trans-1,4-cyclohexanedimethanol.

Substance C comprises 16.3% of cis-1,4-CHDM and 83.7% of trans-1,4-CHDM.

Substance C was distilled under the same conditions as shown in Example 1 except that it was distilled under the conditions of "number of theoretical plates" of 10 plates. 30 g of Distillate Ca was obtained, which comprises 9.0% of cis-1,4-CHDM and 91.0% of trans-1,4-CHDM.

EXAMPLE 4

A mixture of 50 g of Raw material (a) and 0.5 g of sodium methylate was put in an eggplant type flask of 100 ml and was heated in an oil bath at a temperature of 180° C. for one hour, while stirring, and then cooled to room temperature to obtain Substance D including prevailingly trans-1,4-cyclohexanedimethanol.

Substance D comprises 14.8% of cis-1,4-CHDM and 85.2% of trans-1,4-CHDM.

Substance D was distilled under the same conditions as shown in Example 2 except that it was distilled under the conditions of "number of theoretical plates" of 10 plates. 30 g of Distillate Da was obtained, which comprises 8.6% of cis-1,4-CHDM and 91.4% of trans-1,4-CHDM.

EXAMPLE 5

3 kg of Raw material (b) was put in a 5 liter flask and distilled in a rectification tower (having "number of theoretical plates" of 20 plates, length of one meter and diameter of 30 mm, and containing Raschig ring) under the conditions of a reduced pressure of 10 mmHg and temperatures of 152° to 163° C. 0.72 kg of Distillate Ea and 2.00 kg of Distillate Eb were separately obtained.

Distillate Ea comprises 3.4% of cis-1,4-CHDM and 96.6% of trans-1,4-CHDM, while Distillate Eb comprises 33.2% of cis-1,4-CHDM and 66.8% of trans-1,4-CHDM.

A mixture of 2 kg of Distillate Eb and 80 g of a 50% aqueous solution of NaOH was put in a 3 liter flask with agitator and slowly heated to 180° C. and heated at a temperature of 180° C. for 30 minutes, and then cooled to room temperature. The reaction mixture was neutralized by hydrochloric acid to obtain Substance F.

Substance F comprises 15.8% of cis-1,4-CHDM and 84.2% of trans-1,4-CHDM.

Substance F was put in a 5 liter flask and distilled in the same manner as that mentioned above to obtain 0.64 kg of Distillate Ga and 1.10 kg of Distillate Gb.

Distillate Ga comprises 2.2% of cis-1,4-CHDM and 97.8% of trans-1,4-CHDM.

Distillate Gb comprises 22.2% of cis-1,4-CHDM and 77.8% of trans-1,4-CHDM.

EXAMPLE 6

A mixture of 3 kg of Raw material (b) and 60 g of a 50% aqueous solution of NaOH was put in 5 liter flask and distilled in a rectification tower (having "number of theoretical plates" of 20 plate, length of one meter and diameter of 30 mm, and containing Raschig ring) under the conditions of a reduced pressure of 10 mmHg and temperatures of 153° to 162° C. 0.6 kg of Distillate Ha, 0.8 kg of Distillate Hb and 1.2 kg of Distillate Hc were obtained.

Distillate Ha comprises 3.6% of cis-1,4-CHDM and 96.4% of trans-1,4-CHDM. Distillate Hb comprises 2.4% of cis-1,4-CHDM and 97.6% of trans-1,4-CHDM. Distillate Hc comprises 2.2% of cis-1,4-CHDM and 97.8% of trans-1,4-CHDM.

EXAMPLE 7

A mixture of 800 g of Raw material (b) and 16 g of sodium methylate was distilled in a rectification tower (having "number of theoretical plates" of 20 plates, length of one meter and diameter of 30 mm, and containing Raschig ring) under the conditions of a reduced pressure of 40 mmHg and temperatures of 185° to 188° C. 500 g of Distillate J was obtained.

Distillate J comprises 3.6% of cis-1,4-CHDM and 96.4% of trans-1,4-CHDM (by chromatographic analysis).

Distillate J was poured into a stainless steel tray at a temperature of 70° C., and then allowed to stand over night. Solid thus obtained was cut with a frozen cutter (Type FZ, made by Shonan Industrial Co., Ltd.) to obtain white powders of trans-1,4-CHDM having a melting point of 62° C.

EXAMPLE 8

A mixture of 800 g of Raw material (a) and 8 g of NaOH was put in a stainless steel autoclave of one liter and heated at a temperature of 180° C. for two hours. After cooling, the reaction mixture was distilled in the same manner as that in Example 7 to obtain Distillate K.

Distillate K was poured into a tray, cooled to solid and then crushed to obtain white powders. The powder comprises 3.2% of cis-1,4-CHDM and 96.8% of trans-1,4-CHDM and has a melting point of 62° C.

EXAMPLE 9

A mixture of 800 g of Raw material (b) and 6 g of sodium alcoholate was distilled in a rectification tower (having "number of theoretical plates" of 10 plates, length of 0.5 m, and diameter of 30 mm, and containing Raschig ring) under the conditions of a reduced pressure of 40 mmHg and temperatures of 185° to 188° C. to obtain 500 g of Distillate L.

After Distillate L was kneaded by kneader having jacket (Type PNV-1; made by Irie Shokai Co., Ltd.) for 10 minutes, and then allowed to stand over night, solid thus obtained was crushed with a frozen cutter to obtain white powders of trans-1,4-CHDM. The powder comprises 9.7% of cis-1,4-CHDM and 90.3% of trans-1,4-CHDM, and has a melting point of 58° C.

EXAMPLE 10

A mixture of 800 g of Raw material (b) and 5 g of sodium alcoholate was distilled in a rectification tower (having "number of theoretical plates" of 10 plates, length of 0.5 m, and diameter of 30 mm, and containing Raschig ring) under the conditions of a reduced pressure of 40 mmHg and temperatures of 185° to 188° C. to obtain 500 g of Distillate M.

After Distillate M was kneaded by kneader having jacket for 10 minutes and allowed to stand for one hour, solid thus obtained was shaped with a pelletizing device (Type EXD-100, made by Fuji Powdal Co., Ltd.) to obtain white pellets having length of 10 to 50 mm and diameter of 3 mm. The pellet comprises 3.2% of cis-1,4-CHDM and 96.8% of trans-1,4-CHDM, and has a melting point of 62° C.

What is claimed is:

1. A process of increasing the purity of trans-1,4-cyclohexanedimethanol recovered from a mixture of cis- and trans-1,4-cyclohexanedimethanol, comprising the steps of:

distilling at a temperature of about 150° to 200° C. and under a reduced pressure of 1 to 50 mm Hg a heating mixture of cis- and trans-1,4-cyclohexanedimethanol in the presence of an alkali;

recovering, as the distillate a trans-1,4-cyclohexanedimethanol product from the distilling step, cooling said product to a solid, and subsequently pulverizing said solid to a powder, wherein said product comprises at least 80% of trans-1,4-cyclohexanedimethanol.

2. The process of increasing the purity of trans-1,4-cyclohexanedimethanol as defined in claim 1, wherein said product comprises at least 85% of the trans-1,4-cyclohexanedimethanol.

3. The process of increasing the purity of trans-1,4-cyclohexanedimethanol as defined in claim 1, wherein said product comprises at least 90% of the trans-1,4-cyclohexanedimethanol.

4. The process of increasing the purity of trans-1,4-cyclohexanedimethanol as defined in claim 1, wherein the temperature of said heated mixture is within the range of 150° to 250° C.

5. The process of increasing the purity of trans-1,4-cyclohexanedimethanol as defined in claim 1, wherein said alkali is selected from the group consisting of: sodium hydroxide, lithium hydroxide, potassium hydroxide, alkaline earth metal hydroxides, sodium methoxide, sodium ethoxide and ethanolamine.

6. A process of increasing the purity of trans-1,4-cyclohexanedimethanol recovered from a mixture of cis- and trans-1,4-cyclohexanedimethanol, comprising the steps of:

heating at a temperature of about 150° to 250° C. a mixture of cis- and trans-1,4-cyclohexanedimethanol in the presence of alkali, to obtain a first product which is predominantly trans-1,4-cyclohexanedimethanol, and distilling said first product under reduced pressure of 1 to 50 mm Hg to obtain a second product, as the distillate cooling said second product to a solid and subsequently pulverizing said solid to a powder, wherein said second product comprises at least 80% of trans-1,4-cyclohexanedimethanol.

7. The process of increasing the purity of trans-1,4-cyclohexanedimethanol as defined in claim 6, wherein the temperature at which said mixture is heated is from about 160° to 200° C.

8. The process of increasing the purity of trans-1,4-cyclohexanedimethanol as defined in claim 6, wherein said alkali is selected from the group consisting of: sodium hydroxide, lithium hydroxide, potassium hydroxide, alkaline earth metal hydroxides, sodium methoxide, sodium ethoxide and ethanolamine.

9. The process as defined in claim 6, wherein the purity of said second product is at least 85%.

* * * * *